US008399236B2

United States Patent
Eiden et al.

(10) Patent No.: US 8,399,236 B2
(45) Date of Patent: Mar. 19, 2013

(54) SYSTEM COMPRISING BACTERIOPHAGES AND PARTICLES THAT CONTAIN ACTIVE SUBSTANCES

(75) Inventors: Stefanie Eiden, Leverkusen (DE); Axel Eble, Köln (DE); Martin Weiss, Bornheim / Sechtem (DE); Daniel Gordon Duff, Leverkusen (DE); Olaf Bork, Dunedin (NZ); Holger Egger, Köln (DE); Bastian Budde, Köln (DE); Sascha Plug, Leverkusen (DE)

(73) Assignee: Bayer Technology Services GmbH, Leverkusen (DE)

( * ) Notice: Subject to any disclaimer, the term of this patent is extended or adjusted under 35 U.S.C. 154(b) by 145 days.

(21) Appl. No.: 12/672,096

(22) PCT Filed: Aug. 1, 2008

(86) PCT No.: PCT/EP2008/006336
§ 371 (c)(1),
(2), (4) Date: Feb. 4, 2010

(87) PCT Pub. No.: WO2009/018964
PCT Pub. Date: Feb. 12, 2009

(65) Prior Publication Data
US 2010/0285136 A1    Nov. 11, 2010

(30) Foreign Application Priority Data
Aug. 6, 2007   (DE) .................... 10 2007 036 866

(51) Int. Cl.
  *C12N 7/00*    (2006.01)
(52) U.S. Cl. .................... 435/235.1; 424/93.6; 442/123; 442/121
(58) Field of Classification Search ............... 435/235.1; 424/93.6; 442/121, 123
See application file for complete search history.

(56) References Cited

U.S. PATENT DOCUMENTS 4,282,209 A * 8/1981 Tocker .......................... 514/477
7,700,374 B2 * 4/2010 Shiotsuka et al. ............ 436/525

FOREIGN PATENT DOCUMENTS

WO   03 078451 A2   9/2003
WO   2004 035612 A2   4/2004

OTHER PUBLICATIONS

Brown Kathlynn C, "Hitting the target with bifunctional phage"; Chemistry and Biology Aug. 2004, Previews, 1033-1035.
Chen et al.; "Design and validation of a bifunctional ligand display system for receptor targeting"; Chemistry & Biology, vol. 11, 1081-109, Aug. 2004.
Kalàsz et al; Drug Excipients Current Medicinal Chemistry, 2006, 13, pp. 2535-2563.

(Continued)

*Primary Examiner* — Christopher M Gross
*Assistant Examiner* — Jeremy C Flinders
(74) *Attorney, Agent, or Firm* — Norris, McLaughlin & Marcus, P.A.

(57) ABSTRACT

The present invention concerns a system, comprising bacteriophages and particles comprising active agents, in which a first additional peptide is fused to proteins of the bacteriophage, the first additional peptide adheres to the surface of the particle and furthermore a second additional peptide is fused to proteins of the bacteriophage. The second additional peptide can adhere on substrate surfaces. The present invention furthermore concerns the use of the system for delayed release of active agents and also a method for production of the system. The present invention furthermore concerns a method for the selection of phage species from a combinatorial phage population.

9 Claims, 1 Drawing Sheet

OTHER PUBLICATIONS

Light et al; Phophabs: antibody-phage-alkaline phosphatase conjugates for one step elisa's without immunization: Bioorganic & Medicinal Chemistry Letters, vol. 2, No. 9, 1992, pp. 1073-1078.

Kondo; "Microcapsules—General Concepts"; Microcapsule Processing and Technology, 1979, 1.

Newton et al; "Melanoma imaging with pretargeted bivalent bacteriophage"; Journal of Nuclear Medicine: Official Publication, Society of Nudlcar Medicine; Mar. 2007, vol. 48, No. 3, pp. 429-436.

O'Neil et al; "Phage display: protein engineering by directed evolution"; Current Opinion in Structural Biology, 1995, 5, pp. 443-449.

Sambrook et al; "Molecular cloning: a laboratory manual"; Third Edition, Cold Spring Harbor Press 2001; pp. 1.84-1.87 Protocol 17 "Directional Coloning into plasmid vectors".

Sambrook et al; "Molecular cloning: a laboratory manual"; Third Edition, Cold Spring Harbor Press 2001; Protocol 23 "The Hanahan method for preparation and transformation of competent *E. coli*: high-efficiency transformation".

Sambrook et al; "Molecular cloning: a laboratory manual"; Third Edition, Cold Spring Harbor Press 2001; pp. 18.115-18.122.

Sarikaya M et al.,; "Moleculr biomimetics: nanotechnology through biology"; Nature Materials, 2003, 2, 577-585.

Smith et al; "Libraries of peptides and proteins displayed on filamentous phage", Methods in Enzymology 1993, 217, 228-257.

Allen, "Particle size measurement"; vol. 1, 5th Edition, 1997.

* cited by examiner

SEQUENCE LISTING

<160> NUMBER OF SEQ ID NOS: 21

<210> SEQ ID NO 1
<211> LENGTH: 27
<212> TYPE: DNA
<213> ORGANISM: Artificial
<220> FEATURE:

```
<223> OTHER INFORMATION: primer-bind

<400> SEQUENCE: 1
cggcgttccc atggtgtctt tcgctgc                                27

<210> SEQ ID NO 2
<211> LENGTH: 27
<212> TYPE: DNA
<213> ORGANISM: Artificial
<220> FEATURE:
<223> OTHER INFORMATION: primer-bind

<400> SEQUENCE: 2
gcagcgaaag acaccatggg aacgccg                                27

<210> SEQ ID NO 3
<211> LENGTH: 31
<212> TYPE: DNA
<213> ORGANISM: Artificial
<220> FEATURE:
<223> OTHER INFORMATION: primer-bind

<400> SEQUENCE: 3
gctgtctttc gctgcagagg gtgacgatcc c                           31

<210> SEQ ID NO 4
<211> LENGTH: 31
<212> TYPE: DNA
<213> ORGANISM: Artificial
<220> FEATURE:
<223> OTHER INFORMATION: primer-bind

<400> SEQUENCE: 4
gggatcgtca ccctctgcag cgaaagacag c                           31

<210> SEQ ID NO 5
<211> LENGTH: 59
<212> TYPE: DNA
<213> ORGANISM: Artificial
<220> FEATURE:
<223> OTHER INFORMATION: primer-bind
<220> FEATURE:
<221> NAME/KEY: misc_feature
<222> LOCATION: (17)..(34)
<223> OTHER INFORMATION: n is a, c, g or t

<400> SEQUENCE: 5
cgtcaccctc tgcagcnnnn nnnnnnnnnn nnnnagcagc gaaagacacc atgggaagc    59

<210> SEQ ID NO 6
<211> LENGTH: 19
<212> TYPE: DNA
<213> ORGANISM: Artificial
<220> FEATURE:
<223> OTHER INFORMATION: primer-bind

<400> SEQUENCE: 6
cgttcccatg gtgtctttc                                         19

<210> SEQ ID NO 7
<211> LENGTH: 16
<212> TYPE: DNA
<213> ORGANISM: Artificial
<220> FEATURE:
<223> OTHER INFORMATION: primer-bind

<400> SEQUENCE: 7
```
atcgtcaccc tctgca                                                                          16

```
<210> SEQ ID NO 8
<211> LENGTH: 12
<212> TYPE: PRT
<213> ORGANISM: Artificial
<220> FEATURE:
<223> OTHER INFORMATION: Synthetic Peptide

<400> SEQUENCE: 8

Ile Ser Ser Lys Pro Thr Ser Gln Leu Thr Thr Pro
1               5                   10

<210> SEQ ID NO 9
<211> LENGTH: 6
<212> TYPE: PRT
<213> ORGANISM: Artificial
<220> FEATURE:
<223> OTHER INFORMATION: Synthetic Peptide

<400> SEQUENCE: 9

Ser Thr Thr Arg Leu Arg
1               5

<210> SEQ ID NO 10
<211> LENGTH: 19
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala

<400> SEQUENCE: 10

Ile Ser Ser Lys Pro Thr Ser Gln Leu Thr Thr Xaa Pro Ser Thr
1               5                   10                  15

Thr Arg Leu Arg

<210> SEQ ID NO 11
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala

<400> SEQUENCE: 11

Ile Ser Ser Lys Pro Thr Ser Gln Leu Thr Thr Xaa Xaa Pro Ser
1               5                   10                  15

Thr Thr Arg Leu Arg
                20

<210> SEQ ID NO 12
<211> LENGTH: 21
<212> TYPE: PRT
<213> ORGANISM: Artificial
<220> FEATURE:
<223> OTHER INFORMATION: Synthetic Peptide
<220> FEATURE:
<221> NAME/KEY: misc_feature
```

```
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala

<400> SEQUENCE: 12

Ile Ser Ser Lys Pro Thr Ser Gln Leu Thr Thr Xaa Xaa Xaa Pro
1               5                   10                  15

Ser Thr Thr Arg Leu Arg
                20

<210> SEQ ID NO 13
<211> LENGTH: 22
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala
<220> FEATURE:
<221> NAME/KEY: misc_feature
<222> LOCATION: (15)
<223> OTHER INFORMATION: Xaa is Gly or Ala

<400> SEQUENCE: 13

Ile Ser Ser Lys Pro Thr Ser Gln Leu Thr Thr Xaa Xaa Xaa Xaa
1               5                   10                  15

Pro Ser Thr Thr Arg Leu Arg
                20

<210> SEQ ID NO 14
<211> LENGTH: 23
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala
<220> FEATURE:
<221> NAME/KEY: misc_feature
<222> LOCATION: (15)
<223> OTHER INFORMATION: Xaa is Gly or Ala
<220> FEATURE:
<221> NAME/KEY: misc_feature
<222> LOCATION: (16)
<223> OTHER INFORMATION: Xaa is Gly or Ala

<400> SEQUENCE: 14
```

Ile Ser Ser Lys Pro Thr Ser Gln Leu Thr Thr Xaa Xaa Xaa Xaa
1               5                   10                  15

Xaa Pro Ser Thr Thr Arg Leu Arg
                20

<210> SEQ ID NO 15
<211> LENGTH: 24
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala
<220> FEATURE:
<221> NAME/KEY: misc_feature
<222> LOCATION: (15)
<223> OTHER INFORMATION: Xaa is Gly or Ala
<220> FEATURE:
<221> NAME/KEY: misc_feature
<222> LOCATION: (16)
<223> OTHER INFORMATION: Xaa is Gly or Ala
<220> FEATURE:
<221> NAME/KEY: misc_feature
<222> LOCATION: (17)
<223> OTHER INFORMATION: Xaa is Gly or Ala

<400> SEQUENCE: 15

Ile Ser Ser Lys Pro Thr Ser Gln Leu Thr Thr Xaa Xaa Xaa Xaa
1               5                   10                  15

Xaa Xaa Pro Ser Thr Thr Arg Leu Arg
                20

<210> SEQ ID NO 16
<211> LENGTH: 25
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala
<220> FEATURE:
<221> NAME/KEY: misc_feature
<222> LOCATION: (15)
<223> OTHER INFORMATION: Xaa is Gly or Ala
<220> FEATURE:
<221> NAME/KEY: misc_feature
<222> LOCATION: (16)
<223> OTHER INFORMATION: Xaa is Gly or Ala
<220> FEATURE:
<221> NAME/KEY: misc_feature
<222> LOCATION: (17)
<223> OTHER INFORMATION: Xaa is Gly or Ala
<220> FEATURE:
<221> NAME/KEY: misc_feature

```
<222> LOCATION: (18)
<223> OTHER INFORMATION: Xaa is Gly or Ala

<400> SEQUENCE: 16

Ile Ser Ser Lys Pro Thr Ser Gln Leu Thr Thr Xaa Xaa Xaa Xaa
1               5                   10                  15

Xaa Xaa Xaa Pro Ser Thr Thr Arg Leu Arg
                20                  25

<210> SEQ ID NO 17
<211> LENGTH: 26
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala
<220> FEATURE:
<221> NAME/KEY: misc_feature
<222> LOCATION: (15)
<223> OTHER INFORMATION: Xaa is Gly or Ala
<220> FEATURE:
<221> NAME/KEY: misc_feature
<222> LOCATION: (16)
<223> OTHER INFORMATION: Xaa is Gly or Ala
<220> FEATURE:
<221> NAME/KEY: misc_feature
<222> LOCATION: (17)
<223> OTHER INFORMATION: Xaa is Gly or Ala
<220> FEATURE:
<221> NAME/KEY: misc_feature
<222> LOCATION: (18)
<223> OTHER INFORMATION: Xaa is Gly or Ala
<220> FEATURE:
<221> NAME/KEY: misc_feature
<222> LOCATION: (19)
<223> OTHER INFORMATION: Xaa is Gly or Ala

<400> SEQUENCE: 17

Ile Ser Ser Lys Pro Thr Ser Gln Leu Thr Thr Xaa Xaa Xaa Xaa
1               5                   10                  15

Xaa Xaa Xaa Xaa Pro Ser Thr Thr Arg Leu Arg
                20                  25

<210> SEQ ID NO 18
<211> LENGTH: 27
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (12)
<223> OTHER INFORMATION: Xaa is Gly or Ala
<220> FEATURE:
<221> NAME/KEY: misc_feature
<222> LOCATION: (13)
<223> OTHER INFORMATION: Xaa is Gly or Ala
<220> FEATURE:
<221> NAME/KEY: misc_feature
<222> LOCATION: (14)
<223> OTHER INFORMATION: Xaa is Gly or Ala
<220> FEATURE:
<221> NAME/KEY: misc_feature
```

```
<222> LOCATION: (15)
<223> OTHER INFORMATION: Xaa is Gly or Ala
<220> FEATURE:
<221> NAME/KEY: misc_feature
<222> LOCATION: (16)
<223> OTHER INFORMATION: Xaa is Gly or Ala
<220> FEATURE:
<221> NAME/KEY: misc_feature
<222> LOCATION: (17)
<223> OTHER INFORMATION: Xaa is Gly or Ala
<220> FEATURE:
<221> NAME/KEY: misc_feature
<222> LOCATION: (18)
<223> OTHER INFORMATION: Xaa is Gly or Ala
<220> FEATURE:
<221> NAME/KEY: misc_feature
<222> LOCATION: (19)
<223> OTHER INFORMATION: Xaa is Gly or Ala
<220> FEATURE:
<221> NAME/KEY: misc_feature
<222> LOCATION: (20)
<223> OTHER INFORMATION: Xaa is Gly or Ala

<400> SEQUENCE: 18

Ile Ser Ser Lys Pro Thr Ser Gln Leu Thr Thr Xaa Xaa Xaa Xaa
1               5                   10                  15

Xaa Xaa Xaa Xaa Xaa Pro Ser Thr Thr Arg Leu Arg
                20                  25

<210> SEQ ID NO 19
<211> LENGTH: 11
<212> TYPE: PRT
<213> ORGANISM: Artificial
<220> FEATURE:
<223> OTHER INFORMATION: Synthetic Peptide

<400> SEQUENCE: 19

Ile Ser Ser Lys Pro Thr Ser Gln Leu Thr Thr
1               5                   10

<210> SEQ ID NO 20
<211> LENGTH: 7
<212> TYPE: PRT
<213> ORGANISM: Artificial
<220> FEATURE:
<223> OTHER INFORMATION: Synthetic Peptide

<400> SEQUENCE: 20

Pro Ser Thr Thr Arg Leu Arg
1               5

<210> SEQ ID NO 21
<211> LENGTH: 20
<212> TYPE: DNA
<213> ORGANISM: Artificial
<220> FEATURE:
<223> OTHER INFORMATION: primer-bind

<400> SEQUENCE: 21
ccctcatagt tagcgtaacg                                         20
```

SYSTEM COMPRISING BACTERIOPHAGES AND PARTICLES THAT CONTAIN ACTIVE SUBSTANCES

This application is a 371 of PCT/EP2008/006336, filed Aug. 1, 2008, which claims foreign priority benefit under 35 U.S.C. §119 of the German Patent Application No. 10 2007 036 866.8 filed Aug. 6, 2007.

The present invention concerns a system comprising bacteriophages and particles including active agents. These particles containing active agents are either pure active agent particles or capsules that contain at least one active agent and are hereinafter called "particles" for short. The present invention furthermore concerns the use of the system for the delayed release of active agents and a method for production of the system. The present invention furthermore concerns a method for selection of phage species from a combinatory phage population.

Known methods for bonding of active agents are for example impregnation, covalent binding of the active agent to the surface of a substrate or integration of the active agent in a material and delaying the release of the active agent by means of additives or by integration of prolonged-release formulations such as capsules in the material. A review concerning the bonding of active agents to substrates can be found for example in Kalász and Antal, Current Medicinal Chemistry, 2006, 13, 2535-2563.

Depending on the substrate, the impregnation methods require an intensive and repeated treatment of the substrate, with a higher risk of side effects. Active agents or mixtures of active agents can be washed out by environmental effects or washes if the adherence is inadequate. Depending on the substrate, a covalent chemical bond or integration of particles may moreover be difficult to achieve (hairs, skin) or dangerous to health (textiles).

The combination of an inorganic substrate with biological components for the modification of surface properties is known in biomimetics. Bacteriophages presenting short peptides, selected from a phage library, have for example hitherto been used to precipitate or cut off inorganic materials (WO2003/078451). Hybrid materials consisting of an inorganic substrate and specific polypeptide ligands are used as a potential solution for modification of the substrate surface. The identification of the suitable biological ligand for the substrate (usually a peptide) is time-consuming and expensive, however, and has hitherto been an obstacle to a concrete application. The concept of a bifunctional ligand for binding two inorganic components is referred to in the prior art (see for example Sarikaya et al., Nature Materials, 2003, 2, 577-585). The binding of cells or biomolecules to a polymer substrate, in particular to oxidized chlorine-enriched polypyrrol (PPyCl) or poly(lactate-co-glycolate) (PLGA), by bacteriophages with bifunctional binding properties, has been specifically described for example in WO2004/035612. WO2004/035612 mentions the theoretical possibility of binding drugs by this method to the substrate, but only describes the identification of the polymer-specific phage by so-called biopanning and binding of the phage to the polymer substrate. The further binding to a further substance which is not a biological binding partner of the phage used, such as a drug for example, is not further described, although this binding would also have to be selective and would require precise matching of the ligand to the other binding component.

The problem was therefore to provide a system comprising bacteriophages and particles including active agents, in which the phage adheres to the particle and is furthermore suitable for adherence to a substrate surface.

The solution to this problem according to the invention was that a first additional peptide is fused on proteins of the bacteriophage, the first additional peptide adheres to the surface of the particle and furthermore a second additional peptide is fused on proteins of the bacteriophage.

Active agents are first of all substances or mixtures of substances that have an effect desired by the user on an organism, irrespective of whether the latter is of a human, herbal or other nature. In the linguistic usage of the present invention, proteins of the bacteriophage means gene products of the phage genome which for example build up the shell of the bacteriophage. A first additional peptide is a peptide which is not contained on the natural form of the phage, but is for example presented by means of molecular-genetic manipulations of the phage genome on the phage. The peptide is fused to proteins of the bacteriophage, which means that is linked either N-terminally or C-terminally to the protein via a peptide bond.

Particles comprising active agents within the meaning of the present invention are in particular microparticles that exhibit a particle diameter with a d90 value of the volume-weighted distribution $\geq 0.1$ to $\leq 300$, preferably $\geq 0.3$ to $\leq 100$, especially preferably $\geq 0.5$ to $\leq 30$ micrometres. Particles with such sizes are firstly well-suited for adherence to bacteriophages according to the invention. Secondly, particles of such sizes are advantageous with the procedures described above for the production of microparticles. The d90 value of the volume-weighted distribution is that particle size for which it is true that 90% of the particle volume is formed by particles smaller than or equal to the d90 value. Measurement methods for determination of the volume-weighted distribution are listed for example in Terence Allen: Particle Size Measurement, Kluwer Academic Publishers, Dordrecht/Boston/London 1999, p. 404 et seq. The representation of the results is also indicated in this bibliographic reference or can also take place in accordance with the standard DIN ISO 9276-1.

The first additional peptide has the property of adhering to the surface of the particle. The particle and bacteriophage are consequently connected to each other via the first peptide. The type of bond can for example be a covalent bond, an electrostatic interaction via charged or partially charged functional groups, or a hydrogen bridge bond. If an active agent is encapsulated, one of the components of the capsule binds to the phage. If the active agent occurs as a pure particle of active agent, the phage binds directly to the pure active agent. Both forms of binding are brought together in the present invention under the term "particle".

The second additional peptide is also a peptide which is not contained on the natural form of the phage, but is for example presented by means of molecular-genetic manipulations of the phage genome on the phage. The peptide is fused to proteins of the bacteriophage, which means that it is linked either N-terminally or C-terminally to the protein via a peptide bond. This peptide is intended to make it possible for the phage and thus also the particle comprising active agents to adhere to a substrate surface. The type of bond can for example be a covalent bond, an electrostatic interaction via charged or partially charged functional groups, or a hydrogen bridge bond.

In one embodiment of the present invention the first and/or the second additional peptide exhibit a length of $\geq 4$ amino acids to $\leq 100$ amino acids, preferably $\geq 5$ amino acids to $\leq 50$ amino acids, more preferably $\geq 6$ amino acids to $\leq 20$ amino acids. The peptides can be linear but also looped in structure. Peptides with such a number of amino acids can be readily fused to the phage proteins by means of current molecular-biological methods and are suitable for adhering to surfaces. Examples of such peptides are linear peptides with a length of 7 amino acids, linear peptides with a length of 12 amino acids or looped peptides with a length of 7 amino acids, which are linked by a disulphide bridge between two cysteine residues.

In a further embodiment of the present invention the amino acid sequence of the second additional peptide was determined by panning of a combinatorial phage population on a substrate surface. For the evolutive selection of some phage species from a large combinatorial phage population ("phage display library") on a substrate, a phage display library is usually exposed to a substrate in a buffered aqueous environment, so that the binding of some phages can take place. Non-specifically binding and weakly binding phages are washed off using an aqueous washing buffer. Phages which are still binding after the washing, and which are thus specific, are then detached (eluted) using another aqueous buffer, subsequently called elution buffer. This entire procedure is called "panning". The eluted phages are propagated and exposed to the substrate once again in further panning rounds, until a population of phages that bind well accumulates. Examples of this technique can be found in Sarikaya et al., Nature Materials, 2003, 2, 577-585; O'Neil and Hoess, Current Opinion in Structural Biology, 1995, 5, 443-449; Smith and Scott, Methods in Enzymology 1993, 217, 228-257; Sambrook and Russell (Ed.), 2001, Molecular cloning: A laboratory manual (third edition), Cold Spring Harbor Press, pages 18.115 to 18.122. The amino acid sequence itself, which is responsible for the binding, can be determined by means of genetic engineering or molecular biology methods.

In a further embodiment of the present invention the bacteriophages are of type M13. These phages can be readily changed and are easily obtainable and easy to propagate in culture. They exhibit for example the proteins gpIII, gpV, gpVI, gpVII, gpVIII and gpIX as gene products. It is possible that the first additional peptide is fused to the protein gpIII or gpVIII and the second additional peptide is fused to the protein gpIII or gpVIII. The lengthening of these proteins with additional peptides, i.e. the fusing, can be readily executed on these proteins. It is especially preferable if the protein gpIII is fused N-terminally with a peptide of the sequence ISSKPTSQLTTP (SEQ ID NO: 8) and the protein gpVIII is fused N-terminally with a peptide of the sequence STTRLR (SEQ ID NO: 9).

In a further embodiment of the present invention the active agents are selected from the group comprising insecticides and/or fungicides, preferably imidacloprid, deltamethrin, pemethrin, clotrimazole, bifonazole, preventol and/or trifoxystrobin; and also dexpanthenol. Such active agents benefit especially from the possibility of binding them to a substrate surface.

In a further embodiment of the present invention the particles comprising active agents are encapsulated active agents. In various areas of application, for example in the application of agrochemicals or pharmaceutical active agents, it is desirable to achieve for the purpose of topical treatment a long-term adherence of active agents and as controlled release thereof as possible in for example human beings or plants. To this end microparticles which comprise a matrix or a core, a shell and one or more active agents are linked to the previously described genetically engineered bifunctional bacteriophages.

Particles containing active agents, in particular microparticles, comprise one or more active agents which can be formulated as matrix or core-shell particles. Procedures such as spray-drying, disk spraying, polymerization (interfaces, in situ etc.), coazervation and extrusion with subsequent milling are used to produce such microparticles. Further production procedures are described for example in "Microcapsule Processing and Technology" (Asaji Kondo, ISBN 0824768574, 1979, 1 et seq.).

Examples of such active agents are insecticides such as imidacloprid, deltamethrin or pemethrin and fungicides such as clotrimazole, bifonazole, preventol and trifoxystrobin.

"Matrix" or "shell" for the purposes of the present invention means the substance or mixtures of substances surrounding the active agent. The matrix or shell can comprise the following auxiliary substances in addition to the active agent: binding agents, synthetic macromolecules, fillers, dispersing agents, preservatives, antioxidants, wetting agents, surfactants and/or softeners or plasticizers.

The matrix is of such a nature that the release of the active agent over time is adapted to the particular function.

It is possible that the total weight of the matrix or shell, relative to the total weight of the microparticle, is $\geq 1$ wt % to $\leq 99.9$ wt %, preferably $\geq 5$ wt % to $\leq 90$ wt %, more preferably $\geq 10$ wt % to $\leq 80$ wt %. Such matrix or shell percentages allow bacteriophages according to the invention to adhere to the auxiliary substances and active agents employed.

The matrix can furthermore comprise binding agents, synthetic macromolecules and/or fillers. These have inter alia the function of holding the individual components of the microparticle together in a stable form and/or releasing the active agent or mixtures of active agent in a controlled manner.

Examples of binding agents can be selected from the group comprising cellulose derivatives, microcrystalline cellulose, sodium carboxymethylcellulose, methylcellulose, hydroxypropyl-cellulose, hydroxypropylmethylmethylcellulose, lactose, starch (wheat, maize, potato, rice starch), starch derivatives, sucrose, glucose, mannitol, sorbitol, dicalcium phospate, tricalcium phosphate, bolus, zinc oxide, gelatine, maltodextrins, polysaccharides, oligosaccharides, stearic acid, calcium stearate, shellac, cellulose acetatephthalate and/or hydroxylmethylcellulose phthalate.

Examples of synthetic macromolecules can be selected from the group comprising copolymerisates of dimethylaminoethacrylic acid and neutral methacrylic acid esters, acrylic and methacrylic acid ester copolymerisates with trimethylammonium methacrylate, polymerisates of methacrylic acid and methacrylic acid esters, acrylic acid ethyl ester-methacrylic acid methyl ester-copolymerisate, styrene, acrylnitrile copolymer, polystyrene, polycarbonate, polyester, polyether, polyamides, polyimides, polyureas, polyurethanes, polysulphides, polyvinylpyrrolidone, polyvinylpyrrolidone vinylacetate and/or polyvinyl alcohols.

Examples of fillers can be selected from the group comprising minerals such as clay minerals and/or colloidal silicic acid such as for example kaolin, kaolinite, halloysite, montmorillonite, talcum, bentonite, vermiculite and/or allophane. Minerals furthermore comprise oxides, hydroxides, silicates, carbonates and sulphates of calcium, magnesium, aluminium and titanium.

The matrix can furthermore comprise other auxiliary substances that are selected from the group comprising anion-active surfactants, non-ionogenic surfactants and/or lipids with ester linkage.

Examples of anion-active surfactants can be selected from the group comprising soaps, salts of fatty acids, sodium palmitate, sodium stearate, sodium oleate, sodium salts of fatty alcohol sulphates, sulphoccinates, alkyl naphthalene sulphonates, and/or alkyl sulphates.

Examples of non-ionogenic surfactants can be selected from the group comprising partial fatty acid esters of polyvalent alcohols, partial fatty acid esters of sorbitans, partial fatty acid esters of polyhydroxyethylene sorbitan, polyhydroxyethylene fatty alcohol ethers, polyhydroxyethylene fatty acid esters, ethylene oxide-propylene oxide block copolymers, ethoxylated triglycerides and/or silicone surfactants.

Examples of lipids with ester linkage can be selected from the group comprising glycerides, oils, hydrated oils, semi-synthetic and synthetic glycerides, solid and semi-solid waxes, liquid waxes and/or phosphatides.

These auxiliary substances (binding agents, synthetic macromolecules, fillers, dispersing agents, preservatives, antioxidants, wetting agents, surfactants and/or softeners or plasticizers) can support the adherence of bacteriophages according to the invention to microparticles. In addition, the auxiliary substances can facilitate the dispersion of the microparticles in liquids and control the release of the active agent or mixture of active agent.

In a further embodiment of the present invention the material of the shell of the active agent capsule is selected from the group comprising copolymerisates of dimethylaminoethacrylic acid and neutral methacrylic acid esters, acrylic and methacrylic acid ester copolymerisates with trimethylammonium methacrylate, polymerisates of methacrylic acid and methacrylic acid esters, acrylic acid ethyl ester-methacrylic acid methyl ester-copolymerisate, styrene acrylnitrile copolymer, polystyrene, polycarbonate, polyester, polyether, polyamides, polyimides, polyureas, polyurethanes, polysulphides, polyvinylpyrrolidone, polyvinylpyrrolidone vinylacetate and/or polyvinyl alcohols. These materials can support the adherence of the bacteriophages according to the invention and also favourably affect the release of the active agents.

In a further embodiment of the present invention the system additionally comprises a substrate surface, where furthermore the second additional peptide adheres to the substrate surface. In this way the overall state is described that the bifunctional bacteriophage acts as an adhesion agent between a particle comprising active agents and a substrate surface. The material of the substrate surface is preferably selected from the group comprising polycarbonate, polyester, keratin, hairs, mucous membrane, skin, horn, textiles, cotton, wool, chitin, plants and/or semi-conductors. Such substrate surfaces meet important pharmaceutical and technical applications.

A further object of the present invention is the use of the system according to the present invention for the fixing of active agents on substrates.

A further object of the present invention is the use of the system according to the present invention for the delayed release of active agents.

Underlying the present invention was the further problem of developing a procedure for the selection of phage species from a combinatorial phage population (panning procedure), in which in comparison to the prior art the non-specifically binding and weakly binding phages in particular are more effectively washed off a substrate with a rough surface. The present invention therefore furthermore concerns a method for the selection of phage species from a combinatorial phage population. This comprises the following steps:
  a. A phage display library is exposed to a substrate in a buffered aqueous environment,
  b. Washing of the substrate,
  c. Detachment of the binding phages using an aqueous elution buffer,
where the washing of the substrate takes place with energy input by means of ultrasonics.

What is advantageous in this process is that the detachment of the phages by means of ultrasonics makes it possible to select and detect the phages that bind especially well. In each wash fraction the presence of phages is preferably determined qualitatively for example by means of a plaque assay spot test. With the procedure according to the invention, phage pannings can be carried out inter alia on substrates such as polycarbonate, polyester, keratin, hairs, mucous membrane, skin, horn, textiles, cotton, wool, chitin, plants and/or semi-conductors.

Commercially available M13 phage display libraries are advantageously employed which have a randomized peptide as gpIII fusion protein, in particular as a linear peptide with a length of 7 amino acids, as a linear peptide with a length of 12 amino acids, or as a looped peptide with 7 amino acids, which are linked by a disulphide bridge between two cysteine residues. Also conceivable is a combinatorial phage display library created by specific genetic engineering, which has a randomized peptide as gpIII fusion protein that exhibits a different length than 7 or 12 amino acids. Alternatively a combinatorial phage display library which contains randomized peptides fused on the gpVIII protein of the M13 bacteriophage can be created by specific genetic engineering of the phage DNA.

The elution conditions are preferably also adapted to the substrate or particle in question, in order to detach the phages that bind well completely from the surface. The elution can be performed in a gentle manner by addition of an aqueous elution buffer, in which intact phages are obtained. To this end the following parameters can be optimized:

pH value of the elution buffer usually pH 2 to pH 11.5, where the pH of the wash buffer is closer to pH 7 than the pH of the elution buffer, and preferably at least two elution operations are carried out with different elution buffers. At least one acidic and at least one basic elution operation are preferably carried out.

Nature and concentration of the elution buffer substance, such as alkaline phosphates for example (usually in concentrations from 0.005 to 1.5 mol/L), Tris-HCl (0.005 to 1.5 mol/L), glycine HCl (0.05 to 0.2 mol/L) or triethylamine (0.05 to 0.2 mol/L).

Presence, nature and concentration of salts, in particular alkaline or alkaline earth halides, sulphates, carbonates, phosphates or nitrates, preferably sodium chloride usually in concentrations from 5 to 500 mmol/L, preferably 25 to 250 mmol/L, especially preferably 50 to 200 mmol/L.

Presence, nature and concentration of detergents, preferably Tween®-20, sodium dodecyl sulphate (SDS), or Triton X-100, usually in concentrations from 0.01 to 1 wt %, preferably 0.05-0.5 wt %.

Quantity of the elution buffer usually from 1 to 10 mL, temperature of the elution buffer usually 4° C.-55° C., preferably from 15 to 40° C., duration of the elution preferably at least 5 s, Successive elutions can be carried out with the same or different conditions, and the number of these elutions can be adjusted (e.g. one elution with 0.1 mol/l glycine pH 2.0 followed by a neutralization step with 1 mol/l Tris-HCl pH 8, followed by a second elution with 0.1 mol/l triethylamine pH 11.5 followed by a neutralization step with 1 mol/l Tris-HCl pH 7.5).

The method according to the invention for the above-mentioned adaptation of the washing and elution conditions to the substrate or to the particle results in well binding genetically engineered phages which can be selected in a shorter time from a combinatorial phage library than in hitherto used panning procedures.

The eluted phages are propagated and once again exposed to the substrate or to the particle. If further panning rounds are carried out, preferably under more stringent washing conditions, one obtains a population of specifically binding phages which are characterized in that they present a short peptide on their proteins that are responsible for the binding. The sequence of this peptide chain can be determined by sequencing the phage DNA. This DNA sequence can be used to modify other phages by genetic engineering in such a way that they present bindable peptides as fusion proteins. Especially preferably bifunctional phages which bind with one of the peptides specifically to the particle, and with the other peptide specifically to the substrate, are produced in this way.

The present invention furthermore concerns a method for production of a system according to the present invention in which in a phage of type M13, preselected by panning, with a first additional peptide already fused to gpIII, which imparts binding properties to an active agent particle, a second additional peptide is fused to the gpVIII protein of the same phage clone, with it being possible for the peptides fused to gpIII and gpVIII to be the same or different.

Also conceivable is a method for production of a system according to the present invention in which in a phage of type M13, preselected by panning, with a first additional peptide already fused to gpIII, a second additional peptide which imparts binding properties to an active agent particle is fused to the gpVIII protein of the same phage clone, with it being possible for the peptides fused to gpIII and gpVIII to be the same or different.

One embodiment of the method comprises the following steps:

a. Restriction cleavage sites are introduced into the gpVIII procoat sequence by performing localized mutagenesis on the gpVIII procoat gene, which is located on a plasmid (preferably pUC) between two suitable restriction cleavage sites (preferably PagI and KpnI), b. The mutations from step a) are transferred by recloning from the plasmid into the replicative form (RF) of the M13 genome, preferably in the form of the M13KE vector, c. the replicative form of the phage DNA is cleaved with those restriction enzymes whose cleavage sites were introduced by the mutations from step a), and then serves to assimilate suitable complementary oligonucleotides which at the ends show the corresponding overhang for ligation into the open restriction sites and which code for a second additional peptide sequence.

As a result of the palming and selection process there is preferably already a peptide fused to gpIII which imparts binding properties. In order to achieve bifunctionality, a further peptide which also imparts a binding property is usually fused to the gpVIII protein of the same phage clone by molecular-biological manipulation of the phage genome, with it being possible for the peptides fused to gpIII and gpVIII to be the same or different, so that multiple binding properties can be achieved. In order to achieve this fusion, restriction cleavage sites are first introduced into the corresponding position of the phage genome. For cloning purposes the mutations are first introduced on another plasmid, preferably pUC, which contains the gpVIII procoat gene between two suitable restriction cleavage sites (preferably PagI and KpnI). The introduction of the new restriction cleavage sites into the gpVIII procoat sequence is performed by means of localized mutagenesis (e.g. Sambrook and Russell (ed.), 2001, Molecular cloning: A laboratory manual (third edition), Cold Spring Harbor Press, pages 8.42 to 8.45) using oligonucleotides with suitable sequences, such as:

```
Mutagenic oligonucleotides
                                        (SEQ ID NO: 1)
    Nco-A5'-CGGCGTTCCCATGGTGTCTTTCGCTGC-3'

(SEQ ID NO: 2)
    Nco-B5'-GCAGCGAAAGACACCATGGGAACGCCG-3'

(SEQ ID NO: 3)
    Pst-A5'-GCTGTCTTTCGCTGCAGAGGGTGACGATCCC-3'

(SEQ ID NO: 4)
    Pst-B5'-GGGATCGTCACCCTCTGCAGCGAAAGACAGC-3'
```

The restriction cleavage sites introduced can be selected from the group comprising: Aar I, Aat II, Acc I, Acu I, Afl II, Age I, Ahd I, Apa I, ApaL I, Asc I, AsiS I, Avr II, BamH I, Bbs I, Beg I, BciV I, Bcl I, BfrB I, Blp I, BmgB I, Bmt I, Bsa I, Bsg I, BsiW I, BspE I, BssH II, BssS I, BstAP I, BstB I, BstE II, BstX I, BstZ17 I, CspC I, EcoN I, EcoR V, Fse I, FspA I, Hinc II, Hpa I, I-Ceu I, I-Sce I, Mfe I, Mlu I, Nco I, Nhe I, Not I, Nru I, Nsi I, PI-Psp I, PI-Sce I, PaeR7 I, PflF I, PflM I, Pme I, Pml I, PshA I, PspOM I, Pst I, Rsr II, Sac I, Sac II, Sal I, SanD I, Sap I, Sea I, SexA I, Sfi I, SgrA I, Sma I, Spe I, Srf I, Stu I, Sty I, Tli I, Tth111 I, Xba I, Xcm I, Xho I, Xma I, Zra I. An NcoI cleavage site is preferably inserted in the signal sequence of gpVIII and a PstI cleavage site in the mature region. These mutations are then transferred by recloning from the plasmid into the replicative faun (RF) of the M13 genome, preferably in the form of the M13KE vector (New England Biolabs). For this purpose the vector is cleaved with suitable restriction enzymes, preferably PagI and KpnI, and the fragment obtained is ligated into the similarly cleaved M13KE vector. For carrying out restriction and ligation steps on double-stranded plasmids see for example Sambrook and Russell (Ed.), 2001, Molecular cloning: A laboratory manual (third edition), Cold Spring Harbor Press, pages 1.84 to 1.87. For carrying out transformations of plasmids in E. coli bacteria see Sambrook and Russell (Ed.), 2001, Molecular cloning: A laboratory manual (third edition), Cold Spring Harbor Press, pages 1.105-1.122.

After introduction of the cleavage sites into the M13 genome, the replicative form of the phage DNA can usually be cleaved with the two restriction enzymes NcoI and PstI and then serves to assimilate suitable complementary oligonucleotides which at the ends show the corresponding overhang for ligation into the open restriction sites and which code for a peptide sequence conferring adherence. The information for this peptide sequence conferring adherence can originate from the panning procedure of the gpIII phage display library on a suitable substrate. By ligation of the DNA and transformation into suitable host bacteria, bifunctional phages which if necessary present different peptide sequences conferring adherence both on their gpIII and on their gpVIII proteins can be produced.

Alternatively, instead of oligonucleotides which code for a peptide sequence conferring adherence, library oligonucleotides can also be ligated into the suitably cleaved M13 genome. These are usually two complementary oligonucleotides which at the ends show the corresponding overhang for ligation into the open restriction sites. In addition they have a range of usually 15 bases that are freely variable. By ligation of the hybridized oligonucleotides into the cleaved RF DNA and transformation into suitable host bacteria one obtains a randomized gpVIII phage library. The phages can be selected by the already described panning procedures on substrate surfaces.

The present invention furthermore concerns the use of a peptide of the sequence ISSKPTSQLTT-spacer-PSTTRLR (SEQ ID NOS: 10-18) to confer adherence, where the spacer comprises $\geq 0$ to $\leq 10$ repeat units of the amino acids glycine and/or alanine. In the simplest case the spacer, i.e. the spacer between the specified peptide sequences, is not present. The spacer can, however, also comprise $\leq 10$ or $\leq 5$ repeat units of the amino acids glycine and/or alanine. Where both glycine and alanine are present, they can be arranged in any desired order. The specified sequences ISSKPTSQLTT (SEQ ID NO: 19) and PSTTRLR (SEQ ID NO: 20) correspond to the individual peptides determined in Example 6 below. A peptide is in particular suitable for conferring adherence between a polycarbonate surface and a polyurethane surface.

The present invention is further illustrated below by means of Examples 1 to 6.

EXAMPLES

Example 1

Panning of a Combinatorial Phage Display Library (Ph.D.-12™, New England Biolabs) on a Polyurethane Substrate Polyurethane substrate was produced from a mixture of equivalent quantities of Desmophen® 670 BA and Desmodur® N3300 (Bayer MaterialScience AG), and hardened over 16 h at ambient temperature. 20 mg of the substrate was equilibrated for 10 min in Tris-Buffered Saline (TBS, consisting of 50 mmol/l Tris-HCl pH 7.5, 150 mmol/l NaCl) and incubated for 60 min with $4*10^{10}$ pfu (10 µl of the original library) in 1 ml TBS at ambient temperature. The substrate was washed ten times with 10 ml TBST (TBS plus 0.1 vol.-% Tween-20) in each case (by means of brief vortexing, five minutes' rotation plus 5 s ultrasonic bath). The first elution took place under acidic conditions by immersion of the substrate in 1 ml of 0.1 mol/l glycine pH 2.5 for 10 s with subsequent neutralization of the substrate in 1 ml of 0.1 mol/l Tris-HCl pH 8 for 1 min. The first elution solution was neutralized by addition of 200 µl of 1 mol/l Tris-HCl pH 8. The second elution took place under basic conditions by immersion of the substrate in 1 ml of 0.1 mol/l triethylamine pH 11.5 for 1 min with subsequent neutralization of the substrate in 1 ml of 0.1 mol/l Tris-HCl pH 7.5 for 1 min. The second elution solution was neutralized by addition of 200 µl of 1 mol/l Tris-HCl pH 7.5. The substrate was then preserved in TBST, in order to observe time-dependent detachment effects of non-eluted phages.

Figure 1:
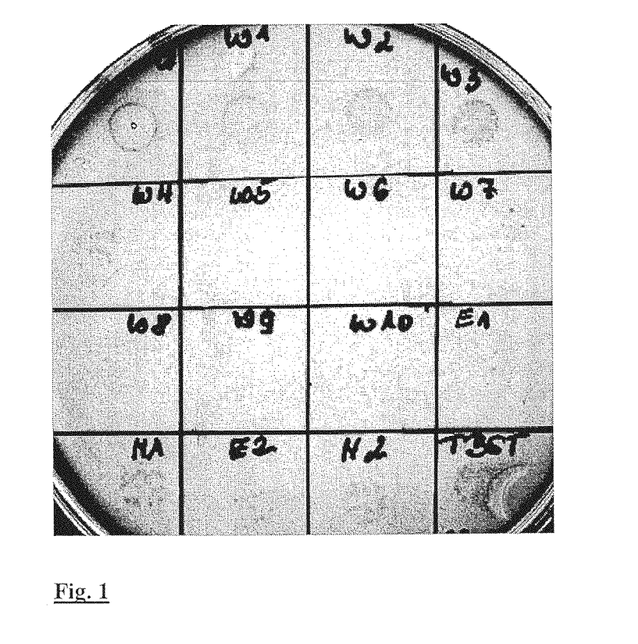
FIG. 1: Plaque assay of panning fractions (Round 1), dripped undiluted onto an LB-Agar-Top inoculated with *E. coli* ER2738 on an LB-IPTG/X-gal plate.
  0: library of Round 1 after the substrate incubation; W1-10: wash fractions 1-10 (use of ultrasonics); E1: elution 1 (acidic); N1: neutralization 1; E2: elution 2 (basic); N2: neutralization 2; TBST: preservation of the substrate piece after panning in TBST.

In each fraction the presence of phages could now be determined qualitatively by means of a plaque assay spot test (see FIG. 1). To this end bacteria of the strain E. coli ER2738 (New England Biolabs) were streaked on an LB Tet agar plate (15 g/l agar, 10 g/l Bacto-Trypton, 5 g/l yeast extract, 5 g/l NaCl, 20 mg/l tetracycline) and incubated over night at 37° C. 10 ml of LB Tet medium (10 g/l Bacto-Tryptone, 5 g/l yeast extract, 5 g/l NaCl, 20 mg/l tetracycline) was inoculated with an individual colony ER2738 and shaken to an $OD_{600}$ of 0.4 at 37° C. 400 µl of it was pipetted in 3 ml of molten LB Agar Top (7 g/l agar, 10 g/l Bacto-Trypton, 5 g/l yeast extract, 5 g/l NaCl) and plated out on an LB-IPTG/X-gal plate (15 g/l agar, 10 g/l Bacto-Tryptone, 5 g/l yeast extract, 5 g/l NaCl, 1.25 mg/l isopropyl-β-D-thiogalactopyranoside, 1 mg/l 5-brom-4-chlor-3-indoxyl-β-D-galactonoside). After hardening, 3 µl of each fraction was dripped onto the plate and this was incubated over night at 37° C. The presence of phages in each fraction was indicated by blue plaques.

The elution fractions (elution 1 and 2 and the two neutralization solutions) were combined and amplified. To this end 10 ml of LB Tet medium was inoculated with 100 µl of an overnight culture ER2738 (in LB Tet) and also the combined elution fractions and shaken for 4.5 h at 37° C. The culture was centrifuged for 10 mM at 4500×g and 4° C., and the supernatant was then centrifuged again. The top ⅘ vol. of the supernatant was mixed with ⅕ vol. PEG/NaCl (20% (w/v) polyethylene glycol 8000, 2.5 mol/l NaCl) and incubated for 1 h at 4° C. The phages were centrifuged off for 20 min at 16000×g and 4° C. and resuspended in 1 ml of TBS (50 mM Tris-HCl pH 7.5, 150 mM NaCl). The solution is centrifuged for 5 min at 10000×g and 4° C., the supernatant is mixed with 200 µl of PEG/NaCl and incubated for 60 min on ice. The phages were centrifuged off for 10 min at 14000×g and 4° C. and resuspended in 200 µl of TBS.

The titre of the phage solution was determined by a plaque assay. To this end 10 ml of LB-Tet medium was inoculated with an individual colony ER2738 and shaken to an $OD_{600}$ of 0.4 at 37° C. 400 µl of it is pipetted into 3 ml of molten LB Agar Top, mixed with 10 µl of a suitable dilution of the phage solution and distributed on an LB-IPTG/X-gal plate. After hardening, the plate was incubated over night at 37° C. The titre of the phage solution (in pfu/ml) could be calculated from the number of blue plaques.

In the following rounds the entire panning procedure was repeated, but $1-2\times10^{11}$ pfu of the amplified eluate is used as a new library, in addition the Tween 20 concentration is raised to 0.5% (v/v).

Three panning rounds in all were carried out. Specifically polyurethane-binding phage clones whose identity could be determined by sequencing the variable range of their genome accumulated in the resultant population. To this end individual phage clones, e.g. from the LB-IPTG/X-gal plate of the titration of the eluate of the third round, were retrieved with an inoculation loop and amplified separately: 2 ml of LB-Tet medium was inoculated with 100 µl of an overnight culture ER2738 (in LB-Tet) and also the phage clone and shaken for 4.5 h at 37° C. The culture was centrifuged for 10 min at 4500×g and 4° C., and the supernatant was then centrifuged again. 1 ml of the phage solution was mixed with 500 µl of PEG/NaCl-Lsg and incubated for 2 h at 4° C. The phages were centrifuged off for 15 min at 14000×g and 4° C. and resuspended in 100 µl of 10 mM Tris-HCl pH 8.0, 1 mM EDTA, 4 M NaI. The DNA was precipitated by 250 µl of ethanol for 10 min and centrifuged off for 15 min at 14000×g and 20° C. The pellet was washed with 70% ethanol, centrifuged for 1 mM at 14000×g and 20° C., dried and resuspended in 30 µl of 10 mM Tris-HCl pH 8.0. The sequencing of the DNA was performed with the primer 5'-CCCTCATAGT-TAGCGTAACG-3' (SEQ ID NO: 21), with the anticodon strand of the M13 DNA being obtained.

Example 2

Unsuccessful Panning of a Combinatorial Phage Display Library (Ph.D.-12™, New England Biolabs) on a Polyurethane Substrate (without Energy Input During the Washing)

Figure 2:
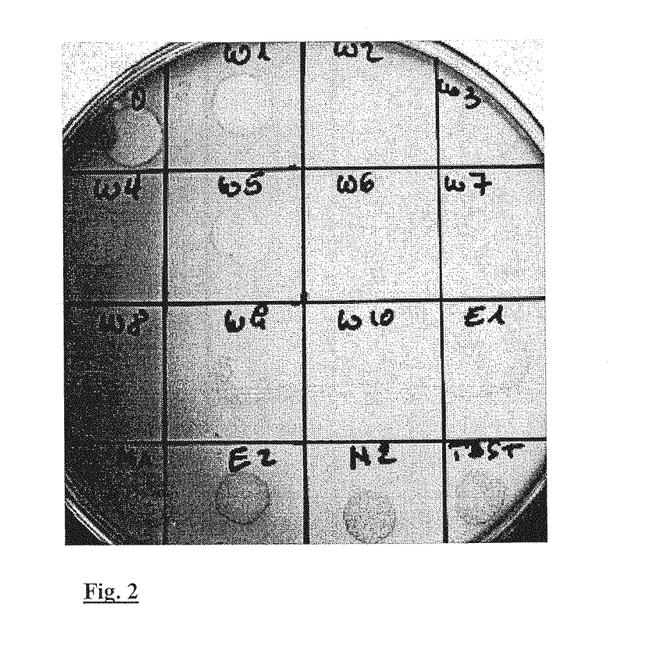
FIG. 2: Plaque assay of panning fractions (Round 1), dripped undiluted onto an LB-Agar-Top inoculated with *E. coli* ER2738 on an LB-IPTG/X-gal plate.
  0: library of Round 1 after the substrate incubation; W1-10: wash fractions 1-10 (without use of ultrasonics); E1: elution 1 (acidic); N1: neutralization 1; E2: elution 2 (basic); N2: neutralization 2; TBST: preservation of the substrate piece after panning in TBST.

The procedure is carried out in a similar way the 1st round of Example 1, except that there was no simultaneous energy input during the washing steps. The fractions obtained were also checked by means of a plaque assay spot test qualitatively for the presence of phages (see FIG. 2).

Example 3

Production of a Combinatorial gpVIII Phage Display Library

To introduce an oligonucleotide bank for the Gene VIII (main shell protein) into the M13 genome, three primers are needed:

```
1. Library oligonucleotide
                                          (SEQ ID NO: 5)
5'CGTCACCCTCTGCAGC(NNN)₆AGCAGCGAAAGACACCATGGGAAGC 2. Extension primer I
                                          (SEQ ID NO: 6)
5' CGTTCCCATGGTGTCTTTC 3. Extension primer II
                                          (SEQ ID NO: 7)
5' ATCGTCACCCTCTGCA
```

A PCR reaction that is used to create the library is first performed on the library oligonucleotide with both extension primers. The library is then digested with NcoI and PstI and inserted into the corresponding restriction sites in a M13KE vector having NcoI and PstI cleavage sites.

So as to be able to introduce the library into the M13 genome, restriction cleavage sites are first introduced into the corresponding position of the genome of M13KE. For cloning purposes the mutations are first introduced on another plasmid (pUC) which contains the gpVIII procoat gene between the restriction cleavage sites PagI and KpnI (pUC-gp8). The introduction of the new restriction cleavage sites into the gpVIII procoat sequence is effected by means of localized mutagenesis (e.g. Sambrook and Russell (Ed.), 2001, Molecular cloning: A laboratory manual (third edition), Cold Spring Harbor Press, pages 8.42 to 8.45) using the following oligonucleotides:

```
Mutagenic oligonucleotides
                                          (SEQ ID NO: 1)
Nco-A5'-CGGCGTTCCCATGGTGTCTTTCGCTGC-3'

(SEQ ID NO: 2)
Nco-B5'-GCAGCGAAAGACACCATGGGAACGCCG-3'

(SEQ ID NO: 3)
Pst-A5'-GCTGTCTTTCGCTGCAGAGGGTGACGATCCC-3'

(SEQ ID NO: 4)
Pst-B5'-GGGATCGTCACCCTCTGCAGCGAAAGACAGC-3'
```

In this way an NcoI cleavage site is inserted in the signal sequence of gpVIII and a PstI cleavage site in the mature region (pUC-gp8mut). These mutations are then transferred by recloning from pUC-gp8mut into the replicative form (RF) of the M13KE genome. For this purpose pUC-gp8mut is cleaved with PagI and KpnI and the fragment obtained is ligated into the similarly cleaved M13KE vector. For carrying out restriction and ligation steps on double-stranded plasmids see for example Sambrook and Russell (Ed.), 2001, Molecular cloning: A laboratory manual (third edition), Cold Spring Harbor Press, pages 1.84 to 1.87. For carrying out transformations of plasmids in E. coli bacteria see Sambrook and Russell (Ed.), 2001, Molecular cloning: A laboratory manual (third edition), Cold Spring Harbor Press, pages 1.105-1.122.

After introduction of the cleavage sites into the genome of M13KE (M13KE-gp8mut), its RF DNA is cleaved with the two restriction enzymes NcoI and PstI and the similarly cleaved library oligonucleotide is ligated into this vector.

Each ligation product is different in the 6 NNN positions and therefore codes for different amino acids at these 6 positions. The ligation mixtures represent the combinatorial gpVIII library and can be used directly for palming on a substrate, in a similar way to a commercial gpIII phage display library (see above).

Example 4

Production of Particles Containing Active Agent by Means of Spray-Drying

In this example the method of spray-drying was used for the production of matrix particles containing active agent on a micro-scale. The production process for encapsulation of the insecticide deltamethrin in a water-insoluble polymer (polystyrene) as matrix is described below.

The dispersion to be sprayed was an O/W emulsion, with the following composition:

O phase: 74% dichloromethane, 18% polystyrene, 8% deltamethrin

W phase: 99% distilled water, 1% alkyl polyglucoside

The deltamethrin and polystyrene were first dissolved in dichloromethane, before this O phase was emulsified into the W phase consisting of distilled water and alkyl polyglucoside (emulsifier) with the aid of an Ultra Turrax of the type IKA T18 with level 5 for about 3 min. The production of the microparticles from the O/W emulsion was effected with the aid of a B-290 spray-drier from the Büchi company. To this end the O/W emulsion was pumped by means of a hose pump (2 g/min) to a binary nozzle (nozzle cap 1.5 mm) and sprayed there with an atomisation gas (nitrogen) 500 L/h. In the spray cylinder the droplets were dried to solid particles with the aid of a drying gas (nitrogen, gas throughput about 31 $m^3$/h), with the entry and exit temperature being 100° C. and 54° C. The solid particles were then separated from the drying gas in a cyclone. The microparticles so obtained consisted of deltamethrine, polystyrene, alkyl polyglucoside and a residual content of solvent (<5 wt %). The particle size distribution of the particles containing active agent, determined by laser diffraction in an aqueous dispersion, showed a d90 value of the volume-weighted distribution of 28 μm.

Example 5

Panning of a Combinatorial Phage Display Library on Particles Containing Active Agent 20 mg of the particles containing active agent from Example 4 was equilibrated for 10 min in TBS and incubated for 60 min with 4*$10^{10}$ pfu of the combinatorial gpVIII library from Example 3 in 1 ml of TBS at ambient temperature. The particles containing active agent were washed ten times with 10 ml of TBST (TBS plus 0.1 vol.-% Tween-20) in each case, being briefly vortexed and incubated for 5 min on a rotator and 5 s in an ultrasonic bath. They were then centrifuged off for 1 min at 14000×g, the supernatant was discarded and the pellet was gathered in new washing buffer with brief vortexing. The first elution took place under acidic conditions by incubation of the particles containing active agent in 1 ml of 0.1 mol/l glycine pH 2.5 for 10 s with subsequent centrifugation (1 min at 14000×g) and neutralization of the particles containing active agent in 1 ml of 0.1 mol/l Tris-HCl pH 8 for 1 min, followed by centrifugation again. The first elution solution was neutralized by addition of 200 μl of 1 mol/l Tris-HCl pH 8. The second elution took place under basic conditions by incubation of the particles containing active agent in 1 ml of 0.1 mol/l triethylamine pH 11.5 for 1 min with subsequent centrifugation (1 min at 14000×g) and neutralization of the particles containing active agent in 1 ml of 0.1 mol/l Tris-HCl pH 7.5 for 1 min, followed by centrifugation again. The second elution solution was neutralized by addition of 200 µl of 1 mol/l Tris-HCl pH 7.5. The particles containing active agent were then preserved in TBST, in order to observe time-dependent detachment effects of non-eluted phages.

In each fraction the presence of phages could now be determined qualitatively by means of a plaque assay spot test. To this end bacteria of the strain *E. coli* ER2738 (New England Biolabs) were streaked on an LB Tet agar plate and incubated over night at 37° C. 10 ml of LB Tet medium was inoculated with an individual colony ER2738 and shaken to an $OD_{600}$ of 0.4 at 37° C. 400 µl of it was pipetted in 3 ml of molten LB Agar Top and plated out on an LB-IPTG/X-gal plate. After hardening, 3 µl of each fraction was dripped onto the plate and this was incubated over night at 37° C. The presence of phages in each fraction was indicated by blue plaques.

The elution fractions (elution 1 and 2 and the two neutralization solutions) were combined and amplified. To this end 10 ml of LB Tet medium was inoculated with 100 µl of an overnight culture ER2738 (in LB Tet) and also the combined elution fractions and shaken for 4.5 h at 37° C. The culture was centrifuged for 10 min at 4500×g and 4° C., and the supernatant was then centrifuged again. The top ⅘ vol. of the supernatant was mixed with ⅕ vol. PEG/NaCl and incubated for 1 h at 4° C. The phages were centrifuged off for 20 min at 16000×g and 4° C. and resuspended in 1 ml of TBS. The solution is centrifuged for 5 min at 10000×g and 4° C., the supernatant is mixed with 200 µl of PEG/NaCl and incubated for 60 min on ice. The phages were centrifuged off for 10 min at 14000×g and 4° C. and resuspended in 200 µl of TBS.

The titre of the phage solution was determined by a plaque assay. To this end 10 ml of LB-Tet medium was inoculated with an individual colony ER2738 and shaken to an $OD_{600}$ of 0.4 at 37° C. 400 µl of it is pipetted into 3 ml of molten LB Agar Top, mixed with 10 µl of a suitable dilution of the phage solution and distributed on an LB-IPTG/X-gal plate. After hardening, the plate was incubated over night at 37° C. The titre of the phage solution (in pfu/ml) could be calculated from the number of blue plaques.

In the following rounds the entire panning procedure was repeated, but $1-2 \times 10^{11}$ pfu of the amplified eluate was used as a new library, in addition the Tween 20 concentration was raised to 0.5% (v/v).

Three panning rounds in all were carried out. Phage clones that bind specifically to the particles containing active agent accumulated in the resultant population. Their identity could be determined by sequencing the variable range of their genome. To this end individual phage clones, e.g. from the LB-IPTG/X-gal plate of the titration of the eluate of the third round, were retrieved with an inoculation loop and amplified separately: 2 ml of LB-Tet medium was inoculated with 100 µl of an overnight culture ER2738 (in LB-Tet) and also the phage clone and shaken for 4.5 h at 37° C. The culture was centrifuged for 10 min at 4500×g and 4° C., and the supernatant was then centrifuged again. 1 ml of the phage solution was mixed with 500 µl of PEG/NaCl-Lsg and incubated for 2 h at 4° C. The phages were centrifuged off for 15 min at 14000×g and 4° C. and resuspended in 100 µl of 10 mM Tris-HCl pH 8.0, 1 mM EDTA, 4 M NaI. The DNA was precipitated by 250 µl of ethanol for 10 min and centrifuged off for 15 min at 14000×g and 20° C. The pellet was washed with 70% ethanol, centrifuged for 1 min at 14000×g and 20° C., dried and resuspended in 30 µl of 10 mM Tris-HCl pH 8.0. The sequencing of the DNA was performed with the primer 5'-CCCTCATAGTTAGCGTAACG-3' (SEQ ID NO: 21), with the anticodon strand of the M13 DNA being obtained.

Example 6

Production of a Bifunctional Bacteriophage that has a Peptide 12 Amino Acids in Length, Fused to gpIII and Binding Specifically to Polyurethane, and Also a Peptide 6 Amino Acids in Length, Fused to gpVIII and Binding Specifically to Polycarbonate As a result of the panning of a commercial phage library (Ph.D.-12™, New England Biolabs) on polycarbonate, a peptide 12 amino acids in length (ISSKPTSQLTTP) (SEQ ID NO: 8), fused to gpIII, and having polycarbonate binding properties, was available in a phage clone ("PC02-11"). In order to achieve bifunctionality, a further peptide 6 amino acids in length (STTRLR)(SEQ ID NO: 9)), having polyurethane binding properties, was fused to the gpVIII protein of the same phage clone. The clone with this sequence ("PUR01-1") was found by panning of a randomized gpVIII phage display library (see above) on polyurethane.

In order to achieve the combination, the replicative form of PUR01-1 was first cleaved with the restriction enzymes PagI and KpnI. The insert that contains the gpVIII gene with fused polyurethane-binding peptide was ligated into the replicative form of PC02-11, which was also cleaved with PagI and KpnI. Bifunctional phages that present different peptide sequences conferring adherence on their gpIII and on their gpVIII proteins were produced by transformation into competent *E. coli* ER2738 bacteria (New England Biolabs).

Figures

The invention claimed is:

1. A composition comprising a bacteriophage and a particle comprising an active agent, wherein the bacteriophage is of Type M 13, wherein a first additional peptide is fused to a protein of the bacteriophage, the first additional peptide is fused to bacteriophage protein gpIII or gpVIII and furthermore a second additional peptide is fused to bacteriophage protein gpVIII or gpIII, and wherein the protein gpIII is fused N-terminally with a peptide of the sequence ISSKPTSQLTTP (SEQ ID NO: 8) and the protein gpVIII is fused N-terminally with a peptide of the sequence STTRLR (SEQ ID NO: 9).

2. Composition according to claim 1, in which the amino acid sequence of the second additional peptide was determined by panning of a combinatorial phage population on a substrate surface.

3. Composition according to claim 1, in which the active agent is selected from the group consisting of insecticides and fungicides.

4. Composition according to claim 1, in which the particle comprising the active agent is an encapsulated active agent.

5. Composition according to claim 4, in which the active agent is encapsulated in a shell of a material selected from the group consisting of copolymerisates of dimethylaminoethacrylic acid and neutral methacrylic acid esters, acrylic and methacrylic acid ester copolymerisates with trimethylammonium methacrylate, polymerisates of methacrylic acid and methacrylic acid esters, acrylic acid ethyl ester methacrylic acid methyl ester copolymerisate, styrene, acrylnitrile copolymer, polystyrene, polycarbonate, polyester, polyether, polyamides, polyimides, polyureaes, polyurethane, polysulphides, polyvinylpyrrolidone, polyvinylpyrrolidon vinylacetate and polyvinyl alcohols.

6. Composition according to claim 1, additionally comprising a substrate surface, in which furthermore the second additional peptide adheres to the substrate surface.

7. Composition according to claim 6, wherein the substrate surface comprises a material selected from the group consisting of polycarbonate, polyester, keratin, hairs, mucous membrane, skin, horn, textiles, cotton, wool, chitin, plants and semi-conductors.

8. Method of fixing an active agent on a substrate, said method comprising fixing the active agent on the substrate with the aid of the composition according to claim 1.

9. Method of delaying the release of an active agent, said method comprising incorporating the active agent in the composition according to claim 1.

* * * * *